(12) United States Patent
Quintanar

(10) Patent No.: US 12,178,955 B2
(45) Date of Patent: *Dec. 31, 2024

(54) SECURING CONTROL OF SETTINGS OF WOUND THERAPY APPARATUSES

(71) Applicant: T.J.Smith and Nephew, Limited, Hull (GB)

(72) Inventor: Felix Clarence Quintanar, Hull (GB)

(73) Assignee: T.J.Smith and Nephew,Limited, Hull (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/378,878

(22) Filed: Oct. 11, 2023

(65) Prior Publication Data

US 2024/0033415 A1 Feb. 1, 2024

Related U.S. Application Data

(63) Continuation of application No. 16/980,970, filed as application No. PCT/EP2019/056704 on Mar. 18, 2019, now Pat. No. 11,806,468.

(30) Foreign Application Priority Data

Mar. 19, 2018 (GB) ...................................... 1804347

(51) Int. Cl.
*A61M 1/00* (2006.01)
*G06F 21/62* (2013.01)

(52) U.S. Cl.
CPC .............. *A61M 1/92* (2021.05); *A61M 1/962* (2021.05); *G06F 21/62* (2013.01); *A61M 1/982* (2021.05);
(Continued)

(58) Field of Classification Search
CPC ............ A61M 1/962; A61M 2205/276; A61M 2205/3331; A61M 2205/502; A61M 2205/60; A61M 5/1723; A61M 1/90
See application file for complete search history.

(56) References Cited

U.S. PATENT DOCUMENTS

| | | |
|---|---|---|
| D239,019 S | 3/1976 | Flinn |
| 4,328,828 A | 5/1982 | Cianci |

(Continued)

FOREIGN PATENT DOCUMENTS

| | | |
|---|---|---|
| DE | 102015215165 A1 | 2/2017 |
| EP | 0883430 B1 | 1/2007 |

(Continued)

OTHER PUBLICATIONS

International Preliminary Report on Patentability and Written Opinion for Application No. PCT/EP2019/056704, mailed on Oct. 1, 2020, 9 pages.

(Continued)

*Primary Examiner* — Jessica Arble
*Assistant Examiner* — Nhu Q. Tran
(74) *Attorney, Agent, or Firm* — Knobbe, Martens, Olson & Bear, LLP

(57) ABSTRACT

Embodiments of secure wound therapy systems and methods for operating the systems are disclosed. In some embodiments, the apparatus includes a pressure source, a user interface, and a locking mechanism. The locking mechanism can be in one of at least two states, the at least two states including a first state in which the locking mechanism physically prevents user adjustment of one or more operational parameters with the user interface and a second state in which the locking mechanism does not physically prevent user adjustment of the one or more operational parameters with the user interface. The locking mechanism can include (Continued)

an authentication key and a receiver configured to receive an authentication input, which may be compared to the authentication key. Providing a sufficiently matching authentication input can transition the locking mechanism from the first state to the second state, permitting adjustments to the one or more operational parameters.

20 Claims, 4 Drawing Sheets

(52) U.S. Cl.
CPC ....... *A61M 1/985* (2021.05); *A61M 2205/276* (2013.01); *A61M 2205/3331* (2013.01); *A61M 2205/502* (2013.01)

(56) References Cited

U.S. PATENT DOCUMENTS

| | | | |
|---|---|---|---|
| 4,498,850 A | 2/1985 | Perlov et al. |
| 4,731,076 A | 3/1988 | Noon et al. |
| D357,735 S | 4/1995 | McPhee |
| 5,514,088 A | 5/1996 | Zakko |
| 5,712,795 A | 1/1998 | Layman et al. |
| 6,027,490 A | 2/2000 | Radford et al. |
| 6,203,291 B1 | 3/2001 | Stemme et al. |
| 6,232,680 B1 | 5/2001 | Bae et al. |
| 6,396,407 B1 | 5/2002 | Kobayashi |
| D475,132 S | 5/2003 | Randolph |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,214,202 B1 | 5/2007 | Vogel et al. |
| D581,042 S | 11/2008 | Randolph et al. |
| D590,934 S | 4/2009 | Randolph et al. |
| 7,608,066 B2 | 10/2009 | Vogel |
| 7,611,500 B1 | 11/2009 | Lina et al. |
| D625,801 S | 10/2010 | Pidgeon et al. |
| 7,857,806 B2 | 12/2010 | Karpowicz et al. |
| D630,313 S | 1/2011 | Pidgeon et al. |
| D630,725 S | 1/2011 | Pidgeon et al. |
| D645,137 S | 9/2011 | Gonzalez |
| 8,021,348 B2 | 9/2011 | Risk, Jr. et al. |
| 8,062,272 B2 | 11/2011 | Weston |
| 8,066,243 B2 | 11/2011 | Svedman et al. |
| 8,070,735 B2 | 12/2011 | Koch et al. |
| D654,164 S | 2/2012 | Cole et al. |
| D660,409 S | 5/2012 | Taggerty et al. |
| 8,215,929 B2 | 7/2012 | Shen et al. |
| 8,216,197 B2 | 7/2012 | Simmons et al. |
| 8,226,620 B2 | 7/2012 | Giezendanner et al. |
| 8,308,714 B2 | 11/2012 | Weston et al. |
| 8,317,774 B2 | 11/2012 | Adahan |
| 8,366,692 B2 | 2/2013 | Weston et al. |
| 8,409,160 B2 | 4/2013 | Locke et al. |
| 8,480,641 B2 | 7/2013 | Jacobs |
| 8,540,688 B2 | 9/2013 | Eckstein et al. |
| 8,641,693 B2 | 2/2014 | Locke et al. |
| 8,668,677 B2 | 3/2014 | Eckstein et al. |
| 8,827,967 B2 | 9/2014 | Lawhorn |
| 8,858,517 B2 | 10/2014 | Pan et al. |
| 8,905,985 B2 | 12/2014 | Allen et al. |
| 9,050,398 B2 | 6/2015 | Armstrong et al. |
| 9,084,845 B2 | 7/2015 | Adie et al. |
| 9,138,531 B2 | 9/2015 | Yodfat et al. |
| 9,199,010 B2 | 12/2015 | Yao et al. |
| D750,222 S | 2/2016 | Chang |
| D750,235 S | 2/2016 | Maurice |
| D757,260 S | 5/2016 | Lombardi, III et al. |
| 9,327,063 B2 | 5/2016 | Locke et al. |
| 9,333,281 B2 | 5/2016 | Giezendanner et al. |
| 9,415,199 B2 | 8/2016 | Tsai |
| 9,427,505 B2 | 8/2016 | Askem et al. |
| 9,445,948 B2 | 9/2016 | Smola |
| D773,658 S | 12/2016 | Bow |
| 9,586,036 B2 | 3/2017 | Masuda et al. |
| D788,293 S | 5/2017 | Eckstein et al. |
| D791,939 S | 7/2017 | Turturro et al. |
| D792,586 S | 7/2017 | Becker |
| 9,737,649 B2 | 8/2017 | Begin et al. |
| D797,275 S | 9/2017 | Evans et al. |
| D802,744 S | 11/2017 | Bjelovuk et al. |
| D813,374 S | 3/2018 | Bjelovuk et al. |
| D814,016 S | 3/2018 | Bjelovuk et al. |
| 9,923,401 B2 | 3/2018 | Jung |
| D815,726 S | 4/2018 | Bjelovuk et al. |
| D815,727 S | 4/2018 | Bjelovuk et al. |
| D820,980 S | 6/2018 | Maurice |
| 10,124,093 B1 | 11/2018 | Francis et al. |
| 10,155,070 B2 | 12/2018 | Childress et al. |
| D842,460 S | 3/2019 | Gierse et al. |
| D851,759 S | 6/2019 | Jones et al. |
| D852,356 S | 6/2019 | Steele et al. |
| D888,225 S | 6/2020 | Askem |
| 12,064,546 B2 | 8/2024 | Askem et al. |
| 2002/0013545 A1 | 1/2002 | Soltanpour et al. |
| 2002/0030002 A1 | 3/2002 | Verkaart et al. |
| 2002/0098097 A1 | 7/2002 | Singh |
| 2002/0161317 A1 | 10/2002 | Risk et al. |
| 2004/0068224 A1 | 4/2004 | Couvillon, Jr. et al. |
| 2005/0234485 A1 | 10/2005 | Seegert et al. |
| 2006/0281398 A1 | 12/2006 | Yokomizo et al. |
| 2007/0219513 A1 | 9/2007 | Lina et al. |
| 2008/0005000 A1 | 1/2008 | Radl et al. |
| 2008/0234641 A1 | 9/2008 | Locke et al. |
| 2009/0216205 A1 | 8/2009 | Ryan et al. |
| 2009/0299306 A1 | 12/2009 | Buan |
| 2010/0022990 A1 | 1/2010 | Karpowicz et al. |
| 2010/0155465 A1 | 6/2010 | Mollstam et al. |
| 2010/0244780 A1 | 9/2010 | Turner et al. |
| 2011/0006876 A1 | 1/2011 | Moberg et al. |
| 2011/0060300 A1 | 3/2011 | Weig et al. |
| 2011/0076170 A1 | 3/2011 | Fujisaki et al. |
| 2011/0196291 A1 | 8/2011 | Vischer et al. |
| 2012/0078181 A1 | 3/2012 | Smith et al. |
| 2012/0109083 A1 | 5/2012 | Coulthard et al. |
| 2012/0289913 A1 | 11/2012 | Eckstein et al. |
| 2013/0012772 A1 | 1/2013 | Gunday et al. |
| 2013/0025692 A1 | 1/2013 | Heide et al. |
| 2013/0053795 A1 | 2/2013 | Coulthard et al. |
| 2013/0131616 A1 | 5/2013 | Locke |
| 2013/0237937 A1 | 9/2013 | Ramella et al. |
| 2013/0270166 A1 | 10/2013 | Locke et al. |
| 2013/0274718 A1 | 10/2013 | Yao et al. |
| 2014/0023533 A1 | 1/2014 | Ishii et al. |
| 2014/0276488 A1 | 9/2014 | Locke et al. |
| 2015/0100045 A1 | 4/2015 | Allen et al. |
| 2015/0174320 A1 | 6/2015 | Grant et al. |
| 2015/0231021 A1 | 8/2015 | Smith et al. |
| 2015/0246164 A1 | 9/2015 | Heaton et al. |
| 2015/0320916 A1 | 11/2015 | Croteau et al. |
| 2015/0352296 A1 | 12/2015 | Yodfat et al. |
| 2016/0015872 A1 | 1/2016 | Luckemeyer et al. |
| 2016/0015957 A1 | 1/2016 | Tieck et al. |
| 2016/0101278 A1 | 4/2016 | Norris et al. |
| 2016/0136339 A1 | 5/2016 | Begin et al. |
| 2016/0213843 A1 | 7/2016 | Despa et al. |
| 2016/0250398 A1 | 9/2016 | Barr et al. |
| 2016/0271305 A1 | 9/2016 | Kurihara et al. |
| 2016/0303358 A1 | 10/2016 | Croizat et al. |
| 2017/0189588 A1 | 7/2017 | Croizat et al. |
| 2017/0189666 A1 | 7/2017 | Sealfon et al. |
| 2017/0216501 A1 | 8/2017 | Armstrong et al. |
| 2017/0224975 A1 | 8/2017 | Peer et al. |
| 2017/0296716 A1 | 10/2017 | Middleton et al. |
| 2017/0319758 A1 | 11/2017 | Eddy et al. |
| 2017/0354767 A1 | 12/2017 | Carr et al. |
| 2018/0001000 A1 | 1/2018 | Herwig et al. |
| 2018/0021178 A1 | 1/2018 | Locke et al. |
| 2018/0104391 A1 | 4/2018 | Luxon et al. |
| 2018/0140466 A1 | 5/2018 | Hunt |
| 2018/0250459 A1 | 9/2018 | Kimball et al. |
| 2018/0308578 A1 | 10/2018 | Armstrong et al. |

(56) References Cited

U.S. PATENT DOCUMENTS

| | | |
|---|---|---|
| 2018/0318476 A1 | 11/2018 | Askem et al. |
| 2019/0021541 A1 | 1/2019 | Kuempel |
| 2019/0167867 A1 | 6/2019 | Adams et al. |
| 2019/0192744 A1 | 6/2019 | Greener et al. |
| 2019/0358372 A1 | 11/2019 | Askem et al. |
| 2020/0121833 A9 | 4/2020 | Askem et al. |
| 2021/0077670 A1 | 3/2021 | Long et al. |
| 2021/0392761 A1 | 12/2021 | Kitagawa et al. |

FOREIGN PATENT DOCUMENTS

| | | |
|---|---|---|
| EP | 3124059 A1 | 2/2017 |
| EP | 3124060 A1 | 2/2017 |
| FR | 2939320 A1 | 6/2010 |
| GB | 1220857 A | 1/1971 |
| JP | S5647279 U | 4/1981 |
| JP | H01101978 A | 4/1989 |
| JP | H0796029 A | 4/1995 |
| JP | 2007218241 A | 8/2007 |
| JP | 6047279 B2 | 12/2016 |
| WO | WO-0061206 A1 | 10/2000 |
| WO | WO-03081762 A1 | 10/2003 |
| WO | WO-2008033788 A2 | 3/2008 |
| WO | WO-2009071924 A1 | 6/2009 |
| WO | WO-2011075706 A1 | 6/2011 |
| WO | WO-2011094410 A2 | 8/2011 |
| WO | WO-2012004298 A1 | 1/2012 |
| WO | WO-2012100624 A1 | 8/2012 |
| WO | WO-2013015827 A2 | 1/2013 |
| WO | WO-2013064852 A1 | 5/2013 |
| WO | WO-2013078214 A1 | 5/2013 |
| WO | WO-2013140255 A1 | 9/2013 |
| WO | WO-2014115819 A1 | 7/2014 |
| WO | WO-2014164655 A1 | 10/2014 |
| WO | WO-2015197462 A1 | 12/2015 |
| WO | WO-2016103031 A1 | 6/2016 |
| WO | WO-2016103033 A2 | 6/2016 |
| WO | WO-2016103035 A2 | 6/2016 |
| WO | WO-2016109048 A1 | 7/2016 |
| WO | WO-2017044138 A1 | 3/2017 |
| WO | WO-2017062042 A1 | 4/2017 |
| WO | WO-2017160412 A1 | 9/2017 |
| WO | WO-2017197357 A1 | 11/2017 |
| WO | WO-2018009873 A1 | 1/2018 |
| WO | WO-2018009880 A1 | 1/2018 |
| WO | WO-2018041854 A1 | 3/2018 |
| WO | WO-2018150263 A1 | 8/2018 |
| WO | WO-2018150267 A2 | 8/2018 |
| WO | WO-2018167199 A1 | 9/2018 |
| WO | WO-2018185101 A1 | 10/2018 |
| WO | WO-2018195101 A1 | 10/2018 |
| WO | WO-2019063467 A1 | 4/2019 |
| WO | WO-2019129581 A2 | 7/2019 |
| WO | WO-2019139829 A1 | 7/2019 |
| WO | WO-2019179943 A1 | 9/2019 |
| WO | WO-2019211730 A1 | 11/2019 |
| WO | WO-2019211731 A1 | 11/2019 |
| WO | WO-2019211732 A1 | 11/2019 |
| WO | WO-2019224059 A1 | 11/2019 |
| WO | WO-2020011690 A1 | 1/2020 |

OTHER PUBLICATIONS

International Search Report and Written Opinion for Application No. PCT/EP2019/056704, mailed on Jun. 27, 2019, 12 pages.

Jenkins R.W., et al., "Mechanisms of Resistance to Immune Checkpoint Inhibitors," British Journal of Cancer, Jan. 2, 2018, vol. 118, https://doi.org/10.1038/bjc.2017.434, pp. 9-16.

Wikipedia, "Battery Charger," retrieved from https://web.archive.org/web/20181109005000/https://en.wikipedia.org/wiki/Battery_charger, on Nov. 9, 2018, 12 pages.

SECURING CONTROL OF SETTINGS OF WOUND THERAPY APPARATUSES

CROSS-REFERENCE TO RELATED APPLICATIONS

This application is a continuation of U.S. patent application Ser. No. 16/980,970, filed on Sep. 15, 2020, which is a U.S. national stage application of International Patent Application No. PCT/EP2019/056704, filed Mar. 18, 2019, which claims the benefit of U.K. Patent Application No. 1804347.1, filed Mar. 19, 2018; the disclosure of each of which is hereby incorporated by reference in its entirety.

BACKGROUND

Embodiments or arrangements disclosed herein relate to methods and apparatuses for dressing and treating a wound with topical negative pressure (TNP) therapy. For example, but without limitation, any embodiments disclosed herein may relate to treating a wound with reduced pressure provided from a pump kit. Although not required, any embodiments of the pump kit can be sterile. As another non-limiting example, any embodiments disclosed herein relate to apparatuses and methods for controlling the operation of a TNP system.

Many different types of wound dressings are known for aiding in the healing process of a human or animal. These different types of wound dressings include many different types of materials and layers, for example, pads such as gauze pads or foam pads. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue edema; encouraging blood flow; stimulating the formation of granulation tissue; removing excess exudates, and may reduce bacterial load and thus reduce the potential for infection of the wound. Furthermore, TNP therapy permits less outside disturbance of the wound and promotes more rapid healing.

SUMMARY

Embodiments of the present disclosure relate to apparatuses and methods for wound treatment. Some of the wound treatment apparatuses described herein comprise a pump system or assembly for providing negative pressure to a wound site. Wound treatment apparatuses may also comprise wound dressings that may be used in combination with the pump assemblies described herein, and connector for connecting the wound dressings to the pump assemblies.

In some embodiments, a negative pressure wound therapy apparatus is disclosed. The apparatus includes a negative pressure source, a connector port, at least one switch disposed at the connector port, and a controller. The negative pressure source provides, via a fluid flow path, negative pressure to a wound. The connector port is in fluid communication with an inlet of the negative pressure source and is fluidically connected either (i) to a canister configured to store fluid aspirated from the wound or (ii) to a wound dressing without a canister between the connector port and the wound dressing. The controller determines, based on a signal received from the at least one switch, whether the canister is positioned in the fluid flow path. The controller also adjusts one or more operational parameters of negative pressure wound therapy. The controller may be communicably coupled with various user interfaces configured to receive user inputs and, in some implementations, to provide indications related to operation or settings of the system to the user.

In some embodiments, the apparatus may include a locking mechanism configured to be in at least two states, in which at least one state prevents, disables, or otherwise at least partially limits alteration of some or all of the operational parameters. For example, when the locking mechanism is set to prevent alteration of some or all of the operational parameters, the locking mechanism may block some or all user inputs from one or more user interfaces other than the user inputs associated with unlocking or transitioning to a state of the locking mechanism that does not prevent alteration of some or all of the operational parameters. In another example, the locking mechanism may allow user inputs attempting to alter some or all of the operational parameters, but deny the attempts as exceeding the allowed interactions with the apparatus. The some or all of the operational parameters can be, for example, a negative pressure setpoint or an operational mode (for instance, continuous operation mode, intermittent operation mode, canister operation mode, or canisterless operation mode). When the locking mechanism is transitioned from one state to another less restrictive state, a user may be able to alter the operational parameters which were previously unalterable by the user in the previous state.

The locking mechanism can include a portion (such as a removable cover or a retractable cover) that may physically prevent a user (such as a patient or an unauthorized clinician) from altering one or more operational parameters when in one state. Subsequent to transitioning from the one state to another state, the locking mechanism may no longer physically prevent the user from altering the one or more operational parameters. For example, the locking mechanism may be used secure a compartment of a therapy device that includes one or more user input elements usable to adjust one or more operational parameters, and upon transitioning of the state of the locking mechanism, the locking mechanism may permit access to the compartment and the one or more user input elements and thus adjustments to the one or more operational parameters. Such a design advantageously, in certain embodiments, may enable a low cost device (such as one without a graphical user interface or a sophisticated security feature) to secure one or more operational parameters.

The locking mechanism may include an authentication mechanism with one or more authentication keys. Accordingly, the apparatus may include a receiver configured to receive the authentication key. The receiver may receive one or more authentication keys in various manners including receiving a mechanical key in a key lock, receiving passcodes from keypads or touchpads, swiping or tagging an electromagnetic key card, or receiving a user's biometric information.

Some embodiments may provide a keypad with which a user may enter a passcode, some embodiments may provide a touchpad or a touch screen presenting symbols that, in sequential combination of the symbols, authenticates a user. Some embodiments may provide an electromagnetic scanner, a radio-frequency-identification (RFID), or a biometric sensor. A biometric sensor may be a fingerprint sensor or a facial recognition sensor (for instance, a camera which may be working in conjunction with an infrared sensor). Some embodiments which receive a related, but not exactly matching authentication inputs (such as a fingerprint in some instances) may utilize computing resources to execute evaluation algorithms. Example evaluation algorithms may include pattern matching algorithms, or other types of input transformation and analysis algorithms. Some algorithms may calculate an associated evaluation score and compare against one or more threshold values or a confidence score to determine whether the authentication input is a satisfactory provision of an authentication key.

In some implementations, the locking mechanism may share user interfaces, computing resources, and/or power source of the apparatus's control board, which a user uses to alter operational parameters. In some implementations, the locking mechanism can be communicatively coupled with the control board, but have its own receiver, computing resource, and/or power source.

A wound therapy apparatus is at least disclosed that includes a housing, a pressure source, a user interface, and a locking mechanism. The pressure source can provide negative pressure via a fluid flow path to a wound dressing and operate according to an operational parameter. The user interface can enable a user adjustment of the operational parameter. The locking mechanism can include an authentication key and a receiver. The receiver can receive an authentication input. The locking mechanism can be in at least two states, the at least two states including a first state in which the locking mechanism physically prevents the user adjustment of the operational parameter with the user interface and a second state in which the locking mechanism physically permits the user adjustment of the operational parameter with the user interface. The locking mechanism can transition from the first state to the second state responsive to a match between the authentication input and the authentication key.

The wound therapy apparatus of the preceding paragraph can include one or more of the following features: When the locking mechanism is in the first state, the locking mechanism can physically prevent at least a portion of the user interface from receiving a user input to adjust the operational parameter. The locking mechanism can include a cover, and the locking mechanism can transition from the second state to the first state by retracting the cover. The locking mechanism can include a cover, and the locking mechanism can transition from the second state to the first state by permitting removal of the cover. The user interface can be positioned in a compartment of the housing, and the locking mechanism can prevent access to the compartment when the locking mechanism is in the first state. The authentication key can be a physical key having a shape, and the receiver can include a slot configured to receive the shape as the authentication input. The authentication key can include an electromagnetic component, and the receiver can receive the authentication input by scanning the electromagnetic component. The user interface may not be a graphical user interface. The operational parameter can include a pressure setpoint, a mode of operation setting, or a pump operation profile. The locking mechanism can periodically check the match of the authentication input and the authentication key. The locking mechanism can transition from the second state to the first state responsive to a passage of a threshold time without the user interface receiving a user input. The locking mechanism can transition from the second state to the first state responsive to a passage of a threshold time without the receiver receiving the authentication input. The housing can support the pressure source, the user interface, and the locking mechanism. The wound therapy apparatus can further include the wound dressing.

A method is at least disclosed that can include: providing negative pressure via a fluid flow path to a wound dressing with a pressure source operating according to an operational parameter; physically preventing a user adjustment of the operational parameter with a user interface while a locking mechanism is in a first state; determining that an authentication input matches an authentication key for the locking mechanism; in response to determining that the authentication input matches the authentication key, transitioning the locking mechanism from the first state to a second state; physically permitting the user adjustment of the operational parameter with the user interface while the locking mechanism is in the second state; and providing negative pressure via the fluid flow path to the wound dressing with the pressure source operating according to the operational parameter after the user adjustment of the operational parameter with the user interface.

The method of the preceding paragraph can include one or more of the following features: The physically preventing the user adjustment of the operational parameter with the user interface can include physically preventing at least a portion of the user interface from receiving a user input to adjust the operational parameter. The method can further include retracting a cover of the locking mechanism responsive to the locking mechanism transitioning from the second state to the first state. The method can further include permitting removal of a cover of the locking mechanism responsive to the locking mechanism transitioning from the second state to the first state. The method can further include transitioning the locking mechanism from the second state to the first state responsive to a passage of a threshold time without the user interface receiving a user input. The method can further include supporting the pressure source, the user interface, and the locking mechanism with a device housing.

Any of the features, components, or details of any of the arrangements or embodiments disclosed in this application, including without limitation any of the pump embodiments and any of the wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which.

DETAILED DESCRIPTION

Overview

Embodiments disclosed herein relate to systems and methods of treating a wound with reduced pressure. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below, for example, 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is farther from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue edema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. TNP therapy can help to stabilize the tissue in the apposed position of closure. A further beneficial use of TNP therapy can be found in grafts and flaps where removal of excess fluid is important and close proximity of the graft to tissue is required in order to ensure tissue viability.

Wound Therapy System

Figure 1:
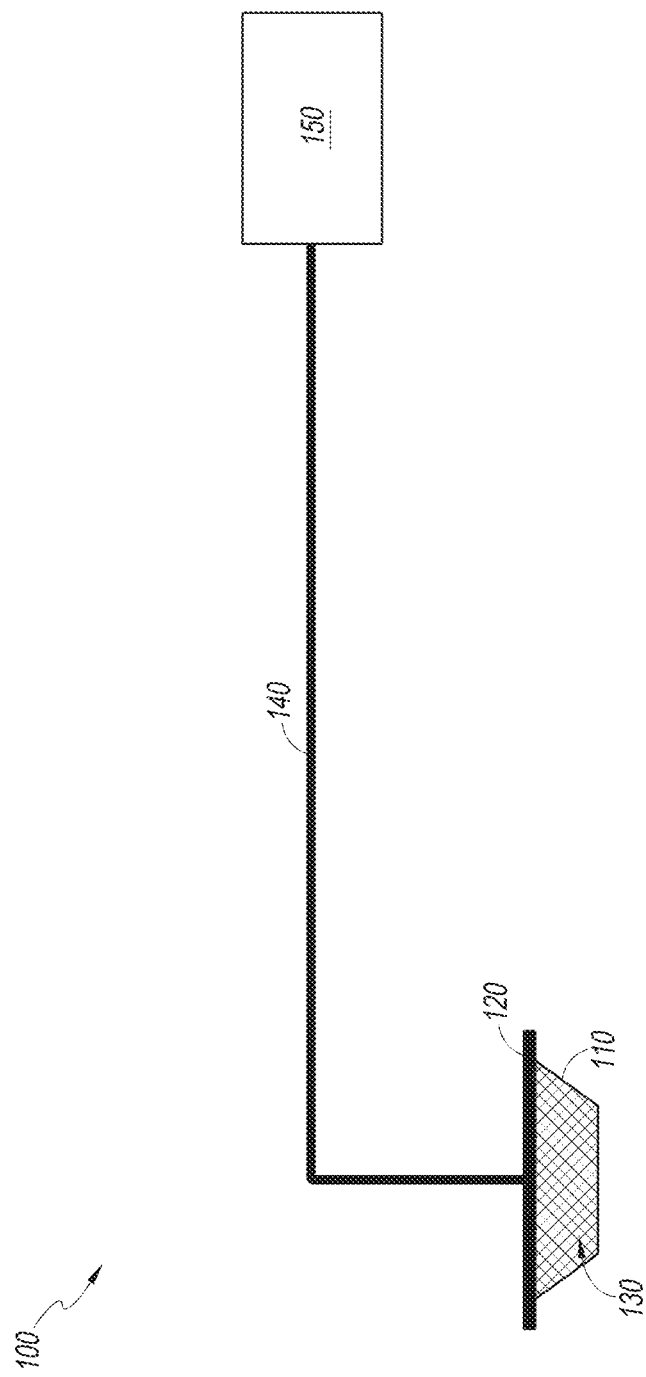
FIG. 1 illustrates a wound therapy system including a pump assembly according to some embodiments.

FIG. 1 illustrates a negative or reduced pressure wound treatment (or TNP) system 100 comprising a wound filler 130 placed inside a wound cavity 110, the wound cavity 110 sealed by a wound cover 120. In some embodiments, one or more of the wound filler 130, the wound cover 120, or any other component, such as a contact layer (not shown), make up a wound dressing. The TNP system 100 includes a negative pressure wound therapy apparatus or a pump assembly 150 configured to provide reduced pressure to the wound. For example, a conduit 140 having at least one lumen can provide a fluid flow path between the pump assembly 150 and the wound. The conduit 140 can have a pump end that is fluidically connected to the pump assembly 150 and a wound end that is inserted under or through the wound cover 120. The conduit 140 can communicate a negative pressure at the pump end to the wound end. The pump assembly 150 may include a canister and operate with the canister, or the pump assembly 150 may operate without a canister.

The pump assembly 150 can operate according to various operational parameters. Some operational parameters may be user-entered. For example, a user-entered operational parameter may be a reduced pressure setpoint. Some operational parameters may be system-default or system-calculated, some of which may be user-adjustable. For example, the reduced pressure setpoint may have had a default or calculated value, but a user may have adjusted the value to facilitate wound therapy.

When a skilled clinician or a caregiver adjusts operational parameters, the adjustments may facilitate wound therapy. However, when a patient or a caregiver who is unfamiliar adjusts the operational parameters, it may deter healing progress. Accordingly, it can be desirable, in certain embodiments, to have access control that prevents, restricts, or limits undesired or unauthorized adjustments. The pump assembly 150 may provide access level authentication before allowing users to adjust one or more operational parameters. The access level authentication may involve a user providing one or more inputs to the pump assembly 150, for example, via a receiver or other user interface.

Figure 2:
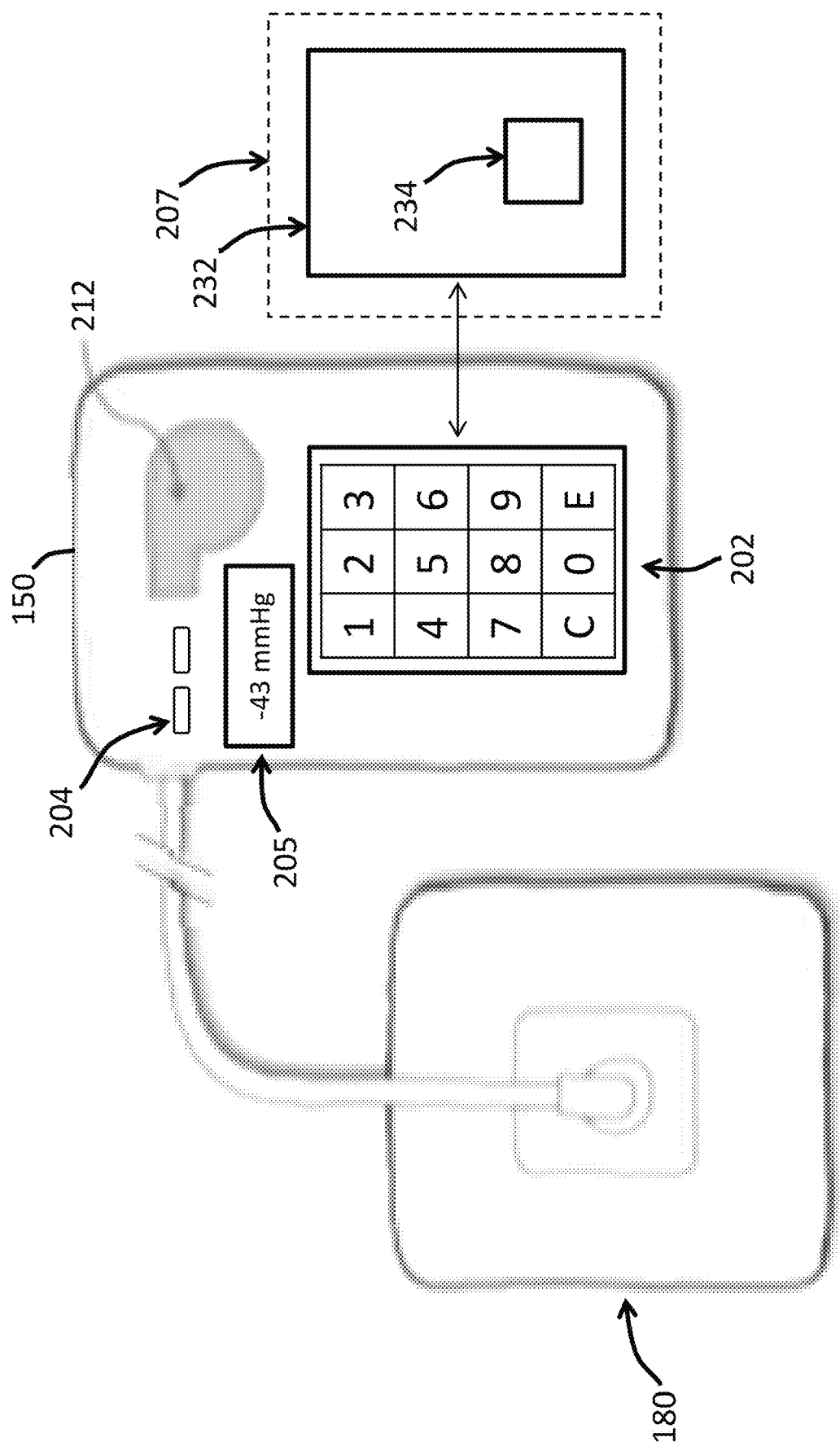
FIG. 2 illustrates a reduced pressure wound therapy system, such as the wound therapy system of FIG. 1 according to some embodiments.

FIG. 2 illustrates an example of the TNP system 100. The pump assembly 150 may include a user interface, which can include one or more input interfaces (such as, switches or buttons 202) and output interfaces (such as, indicators 204 or displays 205). The input interfaces can be used for adjusting, for instance, the operational parameters or validating a user's access level. With regard to the output interfaces, the indicators 204 can communicate to a user of various states of the pump assembly 150 including, for instance, pump assembly status, exudate saturation status of a canister or a wound dressing, remaining power status, and/or user validation status. The displays 205 can communicate various operational settings (as illustrated in FIG. 2 with "−43 mmHg" which may be a measured pressure level or a pressure setpoint) or system statuses. A display may be advantageous, in certain embodiments, in that it can communicate information including operational settings with greater descriptiveness than the indicators 204 or communicate textual status messages such that a user may not utilize a legend for the indicators 204 to interpret system status indications.

One or more input interfaces and one or more output interfaces may be integrated. For example, some or all of the switches or buttons 202, indicators 204, and displays 205 can be provided on a touchpad display. Accordingly, a touchpad is an example interface providing both the input interface and the output interface in an integrated form. There may be more than one user interface configured to provide distinct functionality. For example, a locking mechanism having a biometric sensor, such as a finger print or a facial recognition sensor, may be a separate user interface than the user interface for configuring operational parameters.

The pump assembly 150 can include a locking mechanism 207 usable to physically prevent user access to some or all of the switches or buttons 202. The locking mechanism 207 can include a cover 232 and a receiver 234. The cover 232 can selectively secure to a housing of the pump assembly 150 using one or more fastening mechanisms, such as one or more lockable mechanical fasteners, magnets, or electromagnets. The receiver 234 can receive an authentication input, which can be usable to trigger a transition of the locking mechanism 207 from a locked state to an unlocked state, among other possibilities described herein. The switches or buttons 202 may, in some embodiments, be positioned in a compartment in a housing of the pump assembly 150, and the locking mechanism 207 can be usable to selectively lock the compartment.

When the locking mechanism 207 is in an unlocked state, the cover 232 may not physically prevent user access to some or all of the switches or buttons 202 because the cover 232 can be separated from the pump assembly 150 as illustrated in FIG. 2. Additionally or alternatively, in some implementations, some or all of the cover 232 may retract into a housing of the pump assembly 150 or otherwise change position to permit user access to some or all of the switches or buttons 202.

When the locking mechanism 207 is in a locked state, the cover 232 may cover the switches or buttons 202 to physically prevent user access to some or all of the switches or buttons 202. The cover 232 may be replaced over the switches or buttons 202 by a user or may automatically return from being retracted or otherwise repositioned to cover the switches or buttons 202.

Although the locking mechanism 207 is illustrated in FIG. 2 as being physically separable from the pump assembly 150, the locking mechanism 207 may instead be partially or entirely integrated with the pump assembly 150, such as a housing of the pump assembly 150.

Pump Assembly

Figure 3:
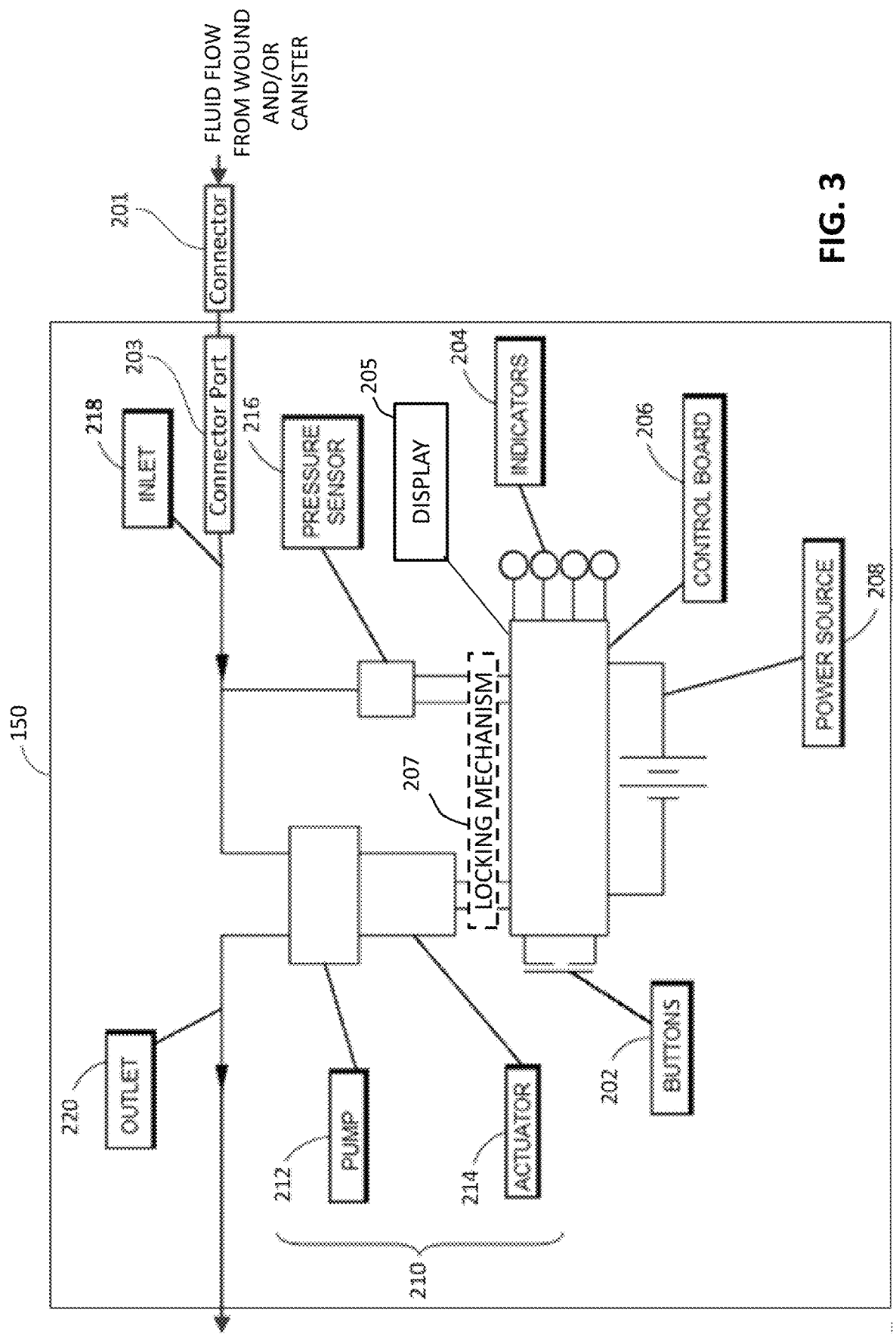
FIG. 3 illustrates a schematic of a pump assembly, such as a pump assembly in the reduced pressure wound therapy system of FIG. 2 according to some embodiments.

FIG. 3 illustrates an example schematic of the pump assembly 150. The pump assembly 150 can include a housing that encloses or supports at least some components of the pump assembly 150. The pump assembly 150 can include one or more input interfaces (such as, the switches or buttons 202, touchpad, or biometric input), one or more output interfaces (such as, the indicators 204 or displays 205), and a control board 206. The input interfaces and output interfaces (which collectively may make up a user interface) can be in communication with the control board 206, which can include one or more controllers and memory. The input interfaces can be used for any suitable purpose for controlling an operation of the pump assembly 150. For example, the input interfaces can be used to activate the pump assembly 150 to provide pressure, pause the pump assembly 150, clear system indicators such as one or more of the one or more of the indications 204, or alter one or more operational parameters like a pressure setpoint or operational mode. The input interfaces can be any type of switch or button, touchpad, touch screen, keyboard, and so on used for providing user inputs. In some embodiments, the input interface can be a press button such as keys of a keypad (or symbols on a touchpad) illustrated in FIG. 2. In various implementations, one or more of the switches or buttons 202 can be included on a touchscreen interface.

The pump assembly 150 can include a connector port 203 adapted to receive a connector 201. The connector 201 can be a part of the canister or the wound dressing that is attached to the pump assembly 150. The connector 201 can be removably attached to the connector port 203. In some arrangements, the connector 201 can be removed from the pump assembly 150 and replaced with another connector that is then attached to the pump assembly 150. For example, the connector 201 that is connected to a RENASYS™ dressing can be removed from the connector port 203 and replaced with another connector that connected to a PICO™ dressing, thereby allowing the pump assembly 150 to be switched from canister to a canisterless mode of operation. The connector 201 and/or pump assembly 150 can be adapted to allow the pump assembly 150 to detect whether the connector 201 is a canister or canisterless connector that is attached to the connector port 203. In some arrangements, the operation of the pump assembly 150 can be adjusted according to whether the pump assembly 150 detects that the connector 201 is a canister or canisterless connector that is connected to the connector port 203.

The connector port 203 can include one or more connector switches in electrical communication with the control board 206, which can include one or more controllers. The one or more connector switches can be configured to engage one or more connectors of the canister or the dressing. The one or more connector switches can permit the pump assembly 150 (e.g., the control board 206) to differentiate between a canister connection and a dressing connection. The connector 201 can include one or more connector switches in addition to or in lieu of the one or more connector switches of the connector port 203. The connector switches contemplated herein can be mechanical, electrical, optical, and/or magnetic, or any other suitable switch, and can include sensors and the like. The connector switches can be configured to close or open an electrical circuit, thereby permitting the control board 206 to detect whether the connector switch is engaged or disengaged. For example, as described in more detail below, the connector port 203 can include a connector switch that is actuated by a portion of the connector 201 that couples a canister to the connector port 203. The connector switch can be further configured so that the switch is not actuated by the connector 201 that couples a dressing to the connector port 203, thereby allowing the control board 206 to detect whether a canister or a dressing is attached to the connector port 203. In some arrangements, the pump assembly 150 can be configured so that the connector switch is activated by the connector 201 that couples a dressing to the connector port 203 and is not activated by the connector 201 that couples a canister to the connector port 203.

With continued reference to FIG. 3, the output interface may include one or more indicators 204 or displays 205. The one or more indicators 204 can indicate one or more operating or failure conditions of the pump assembly 150. Each of the one or more indicators 204 may provide an indication regarding a different operating or failure condition. In some implementations, an active (e.g., lit) indicator of the one or more indicators 204 can represent a certain operation condition for the pump assembly 150. For example, a dressing indicator of the one or more indicators 204 can provide an indication as to presence of leaks in the TNP system 100, and an active dressing indicator can represent a leak. As another example, a dressing capacity indicator of the one or more indicators 204 can provide an indication as to the remaining fluid capacity of the wound dressing or canister, and an active dressing capacity indicator can represent that the wound dressing or canister is at or nearing capacity. As yet another example, a battery indicator of the one or more indicators 204 can provide an indication as to remaining capacity or life of a power source, such as batteries, and an active battery indicator can represent a low capacity. In some embodiments, the one or more indicators 204 can represent a combination of one or more of the above operating or failure conditions of the pump assembly 150 or other operating or failure conditions for the pump assembly 150.

The one or more indicators 204 can be icons. For example, the one or more indicators 204 can be activated (e.g., lit) via an illumination source such as LEDs (not shown) of pump assembly 150. The one or more indicators 204 can, for instance, be of a different color, two different colors (e.g., two indicators can share the same color), or same color. In some embodiments, the pump assembly 150 can include visual, audible, tactile, and other types of indicators or alarms configured to signal to the user various operating conditions. Such conditions may include system on/off, standby, pause, normal operation, dressing problem, leak, error, and the like. The indicators can include speakers, displays, light sources, etc., or combinations thereof. In various implementations, one or more indicators 204 can be included on a touchscreen interface.

Alternatively or additionally, the indicators 204 or the displays 205 can communicate to a user of various operational settings (as illustrated in FIG. 2 with "−43 mmHg") and/or system status. A display may be advantageous, in certain embodiments, in that it can communicate information (including operational settings) with greater descriptiveness than the indicators 204. Additionally, it may also communicate textual status messages such that a status indicator legend for interpretation of the indicator readings may not be utilized. In some implementations, the displays 205 may also provide input interface, such as when a display is a touch screen. In some embodiments, the indicators 204 may be provided on the display 205 as graphical icons.

The pump assembly 150 can be powered by a power source 208, such as a battery power cell or any other suitable power source. The pump assembly 150 can also include a negative pressure source 210, which can include a pump 212 powered by an actuator 214, such as an electric motor. In some embodiments, the actuator 214 is integrated into the pump 212. The negative pressure source 210 can be a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, a pump operated by a voice coil actuator, or any other suitable pump or micropump or any combinations of the foregoing. The pump assembly 150 can include one or more pressure sensors 216 that measure pressure in the fluid flow path.

The pump assembly 150 can further include an inlet 218 to connect the pump assembly 150 to the wound dressing. For example, the inlet 218 can be connected to the connector port 203 and the connector 201 that is in fluid communication with the wound dressing via a fluid flow path.

The pump assembly 150 can also include an outlet 220. The outlet 220 can vent or exhaust gas to the atmosphere. In some embodiments, a filter (not shown) can be interposed between the outlet 220 and the atmosphere. The filter can provide filtration of the gas prior to venting the gas to the atmosphere. The filter can be a bacterial filter, odor filter, or any combination thereof. In some embodiments, a dampening component (not shown), such as a noise dampening component, can be interposed between the outlet 220 and the atmosphere. The dampening component can reduce the noise generated by the pump assembly 150 during operation. In some implementations, the pump assembly 150 can communicate information, such as information related to provision of negative pressure therapy, to one or more remote devices. Such communication can be performed using a wired or wireless interface.

The pump assembly 150 can include a locking mechanism 207. The locking mechanism 207 can be in at least two states, a first state (for instance, a locked state) and a second state (for instance, an unlocked state) in which a first state prevents, disables, or limits alteration of some or all operational parameters while a second state permits alteration of the some or all operational parameters.

The locking mechanism 207 may prevent the control board 206 from adjusting various operational parameters, including, the operational parameters related to the operation of the pump 212, the actuator 214, and/or the pressure sensor 216. For example, the locking mechanism 207 may prevent the control board 206 (and by extension, a user) from altering a negative pressure setpoint. In other words, each state may have an associated list of alterable (or unalterable) operational parameters and setting of the locking mechanism to a particular state prevents or permits adjusting operational parameters of the associated list. Additionally or alternatively, the locking mechanism 207 may be a physical block that selectively prevents user alterations of various operational parameters, including, the operational parameters related to the operation of the pump 212, the actuator 214, and/or the pressure sensor 216.

The prevented or restricted alteration may be associated with one or more ranges (e.g., the state-associated list contains ranges). For example, a state may allow a user to alter the pressure setpoint between −1 mmHg to −40 mmHg, but not below −40 mmHg. Another state may allow a user to alter the pressure setpoint down to −60 mmHg, but not below −60 mmHg. The locking mechanism 207 may prevent alterations of other types of operational parameters including, configuring the pump assembly 150 from operating in a continuous operational mode, intermittent operational mode, canister mode, canisterless mode, and/or operating with a certain type of wound dressing. The locking mechanism 207 may prevent the pump assembly 150 from using a certain treatment-related profile, such as preventing setpoint above −40 mmHg for two weeks or gradually lowering negative pressure over time. Each of the operational parameter configurations may be associated with one or more states, and the locking mechanism 207 may have more than two states, each with own associated list of restrictions.

The locking mechanism 207 may control the transitions between, or among, the states with a receiver and one or more associated authentication keys. The receiver can be configured such that it can receive one or more matching associated authentication keys. In some embodiments, a receiver may be a mechanical key lock with an associated physical key having cut grooves, ridges, and/or troughs. When the key is inserted into the receiver (and in some instances, further rotated), the locking mechanism may transition from one state to another. The receipt of the authentication key transitions the locking mechanism 207 from a more restricted state to a less restricted state. Where there are more than two states, there may be multiple keys associated other states. For example, there may be a 'master key' that allows all or substantially all alteration of operational parameters, and there may be one or more lesser keys that allow narrower range (in number of alterable operational parameters or range of alteration of the operational parameters) of alterations.

A receiver may be touch-input type, such as a touchpad display and the authentication key may be an input of symbols received from the touchpad display. The authentication key made of symbols may be a sequence of symbols where the sequence of symbols may be an alphanumeric passcode, such as "38475" or "PA55WORD!", or a pattern formed by the sequence of symbols, such as the "connect dots in a certain order" type of passcode. In some implementations, the authentication key may be selection of certain symbols, such as selecting picture tiles that show road signs.

A receiver and an authentication key may include an electromagnetic reader and an electromagnetic component, such as a magnetic strip containing passcode. Such authentication key may be a key card that can be swiped or read when in vicinity of a reader, such as an RFID or a near-field communication (NFC) reader. The system may include a corresponding reader as a receiver to receive the authentication key contained within the electromagnetic authentication key.

A receiver may take a biometric input from a biometric sensor, such as from a fingerprint sensor or a facial recognition sensor. A biometric sensor may rely on one type of sensor, such as a fingerprint sensor, or a combination of sensors, such as a camera working in conjunction with an infrared sensor, to detect user input. The locking mechanism 207 may utilize computing resources for execution of matching algorithms (such as pattern matching, or other types of input transformation and analysis algorithms) to determine whether the user input is sufficiently satisfactory for transition between states. The locking mechanism 207 may transition from one state to another upon entry of the correct authentication key.

In some embodiments, the transition may last until a removal of the authentication key. For example, where a mechanical key insertion provides the transition of the states, a removal of the key would cause the system to transition back into its state before the key insertion. In some embodiments, the transition may last for a defined time. The defined time may be user configurable. For example, a biometric input, such as a satisfactory fingerprint, may cause a transition from a more restrictive state to a less restrictive state for five minutes, and the five minutes duration may be configured and increased to ten minutes. In some embodiments, alteration of specific operational parameters may cause a transition from a less restrictive state to a more restrictive state. For example, one adjustment to a pressure setpoint may trigger a state transition.

Each state may be associated with a different access level corresponding to a user's role or expertise. For example, a clinician may have authentication key to enter one state while a caregiver may have authentication key to enter another state. A patient may, in some instances, not have an authentication key at all. Additionally, each state may be associated with different access level corresponding to a different environment. For example, a caregiver who is treating a patient in a home care environment may have different authentication key corresponding to a different state than a same caregiver who is treating a patient in an ambulatory environment associated with another state.

In some embodiments, a state of the locking mechanism 207 is saved in memory so that the control board 206 may interrogate the locking mechanism 207 for its state when a request to alter one or more of the operational parameters is received. If the interrogation result (the state of the locking mechanism 207) indicates that the alteration is permitted, the control board 206 may make the alteration. In some embodiments, the locking mechanism 207 may thus serve as an intermediary between the control board 206 and the various components associated with the operating parameters, and allow adjustments to one or more operating parameters when the locking mechanism 207 is in a state allowing for requested adjustments.

The pump assembly 150 can include one or more of the following features: A user may change various operating parameters, such as the pressure setpoint, and/or indicator parameters, such as alarm and/or alert thresholds, of the pump assembly 150 via the switches or buttons 202. The pump assembly 150 may automatically adjust alarm and/or alert thresholds based on the lock/unlock state. The pump assembly 150 may prompt a user to set alarm or alert thresholds upon, during, or at exit of the unlocked state. The pump assembly 150 may activate alarm and/or alert in response to identifying a transition to the locked state by locking mechanism 207 such that patient safety can be ensured in the locked state.

The pump assembly 150 may include a network interface (not shown) that can be used to connect the pump assembly 150 to a server, cloud, or computing system. The network interface may be wired interface, such as Ethernet, or wireless interface, such as Wi-Fi® or Bluetooth®. Via the network interface, the pump assembly 150 may report its lock state, operating parameters, or alarms and/or alerts to the server, cloud, or computing system. The reporting may be made using an electronic message, such as SMS, e-mail, push notifications on mobile devices, a warning on a GUI of an application, etc. The reporting may include activating some visual and/or acoustic alarms and/or alerts on a remote system.

The pump assembly 150 may host a server application to which a remotely located system, such as a caregiver's workstation or a mobile device, may inquire the lock state (state), operating parameters (settings), or alarms and/or alerts (status) via the network interface. Such reporting and/or inquiry may be executed periodically or upon request. A receiving computer or a caregiver can verify the reported or inquired state, settings, and status against patient prescription and/or desired state, settings, and status.

A caregiver may configure the pump assembly 150 for a therapy and record the operating parameters and/or alarm or alert thresholds in a memory of the pump assembly 150 or in a memory in the locking mechanism 207. Such recording may occur when the caregiver confirms or actuates the locked state, thereby preventing further configuration by others. Any subsequent deviation from the recorded configuration by the pump assembly 150 may cause a comparison logic in the pump assembly 150 to trigger alarms and/or alerts. Detection or indication of wrong or inadequate state, settings, and/or status can result from a failure of the locking mechanism 207 (e.g., such as tempering with the pump assembly 150) or system malfunction. Therefore, the pump assembly 150 can alert the caregiver to immediately attend to the patient and the pump assembly 150.

The pump assembly 150 may analyze the nature of the deviation or quantify the magnitude of the deviation to determine severity of the wrong state. If the severity of the wrong state indicates a situation critical to the patient safety, the pump assembly 150 can stop the therapy, report the situation to a server or a cloud, and/or set the alarms or alerts.

The locking mechanism 207 may share or communicate with the power source 208, computing power (the control board 206), and output interface (the indicators 204 and the display 205). The locking mechanism 207 may be positioned between the pump 212, actuator 214, pressure sensor 216, or other operational components such that it prevents unauthorized access to the operational parameters of one or more of the components. When a proper authentication key is provided to the locking mechanism 207, it may transition from more restrictive state to a less restrictive state to allow alteration of some or all of the operational parameters. In some embodiments, the more restrictive state may completely disable any user inputs from the user interface (such as the buttons 202) such that a user cannot provide any alteration to any operational parameters.

The locking mechanism 207 may have or not share independent power source, computing power, or output interface with one or more other components of the pump assembly 150. Where electronic authentication key is used, the authentication keys or validation mechanism may be stored in an independent electronic circuitry such that a malfunction on the control board 206 cannot affect access management the locking mechanism provides. For example, a mechanical key authentication system, an electromagnetic component authentication system, or a biometric authentication system that do not share the same user interface for altering operational parameters may be considered such compartmentalized access control systems. In certain embodiments, the locking mechanism 207 may provide enhanced security from having a designated access control component positioned in between the normal operational components.

The control board 206 (e.g., a controller) can adjust one or more operational parameters of negative pressure wound therapy depending on whether the pump assembly is connected to the canister or the dressing. For example, in canisterless mode, the level of negative pressure provided to the wound can be reduced compared to canister mode because the wound is exuding a smaller amount of fluid. As another example, detection of one or more operating conditions can be enabled, disabled, or adjusted. For instance, in canisterless mode, canister full detection (or blockage detection) and alarming can be disabled and, instead, dressing full detection and alarming can be enabled.

Figure 4:
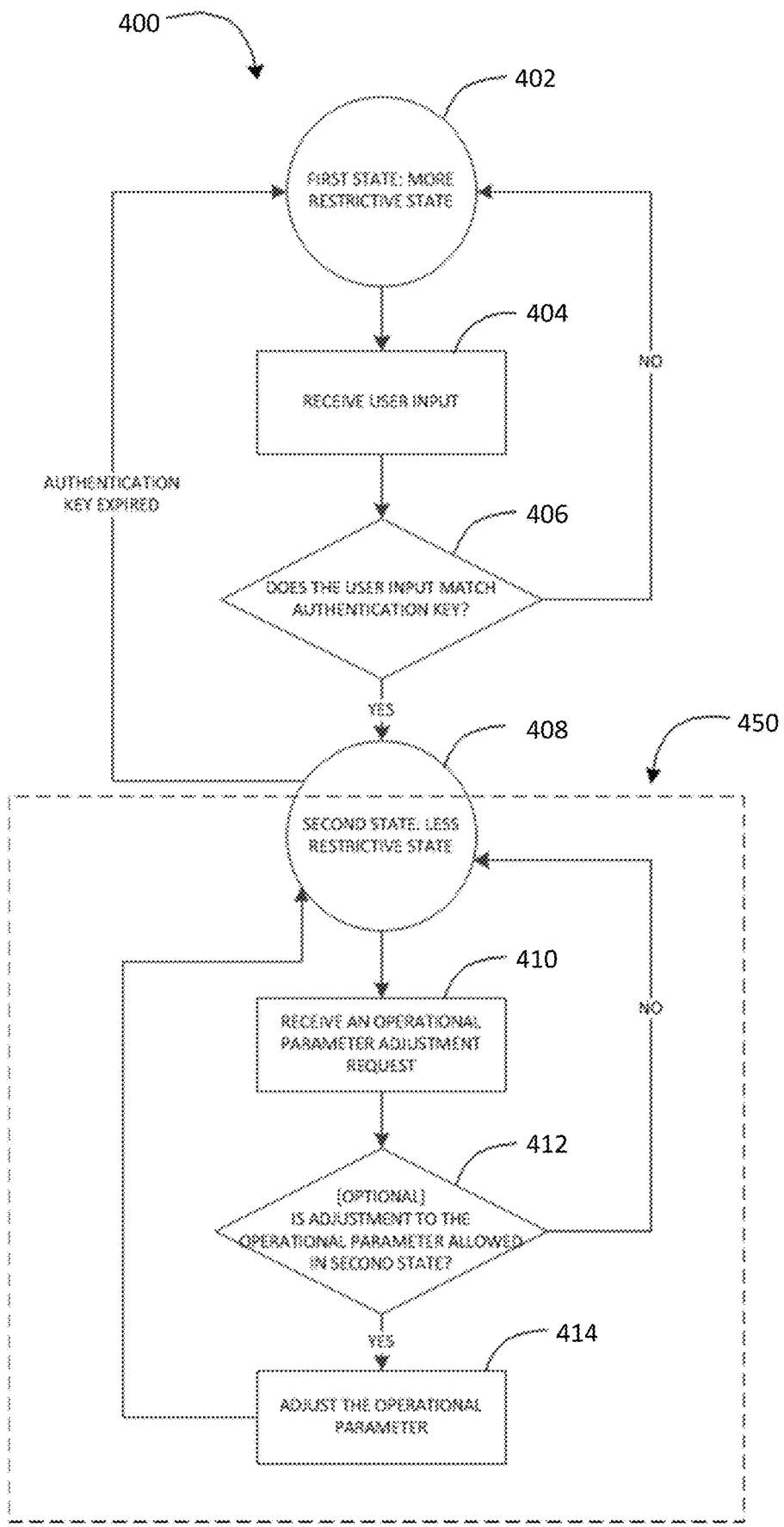
FIG. 4 illustrates an operational state diagram of a wound therapy system, such as the reduced pressure wound therapy system of FIG. 2 according to some embodiments.

FIG. 4 illustrates a state diagram 400 of operations of a TNP system, such as the TNP system 100, according to some embodiments. The state diagram 400 includes a more restrictive first state 402 and a less restrictive second state 408, but a person skilled in the art may appreciate that there may be more than two states. The states and the transitions between may, for example, be implemented by a control board of a therapy device, on a separate electronic circuit, or with a cover that mechanically locks and physically prevents user inputs.

The bottom half 450 of the state diagram 400 relates to the locking mechanism working in conjunction with or alongside the controller of the pump assembly to provide adjustments to various operational parameters. Some aspects of the operational parameter adjustments are illustrative of how the system may treat or permit adjustment requests when in the first state 402 (for instance, block 410 and the denial path of block 412).

The first state 402 prevents, disables, or limits users from adjusting one or more operational parameters. If the state is the first state 402, the system may deny the adjustment request or a user may be physically prevented from adjusting the one or more operational parameters. A display may indicate that the locking mechanism is in the first state or prompt the user to provide the authentication key to transition to the second state 408.

The locking mechanism may transition from the first state 402, which can be more restrictive, to the second state 408, which can be less restrictive, once it receives an authentication key. At block 404, the locking mechanism receives a user input, such as with a receiver. At block 406, the locking mechanism compares the received user input against a stored authentication key to see if there is a match (or, in cases of biometric inputs, a match is sufficiently satisfactory). If there is a match, the locking mechanism transitions to the second state 408. If there is no match, then the locking mechanism remains in the first state 402. When there is a mismatch, the system may notify the user of the mismatch through some output interface, such as the display.

The second state 408 of the locking mechanism may revert back to the first state 402 when the authentication key expires. In some embodiments, the authentication key expiration may be a timeout condition, such as receiving no new authentication request for ten minutes or another duration of the time. In some embodiments, the expiration may be based on removal of the user input, such as removal of a physical key from a key lock interface. Additionally, as the locking mechanism activates in the first state 402, a manual reboot, a reboot from a power failure, or a reboot from detection of a critical error status may also revert the locking mechanism into the first state 402.

Once the locking mechanism is in the second state 408, the system may allow adjustments to one or more operational parameters it previously prevented, disabled, or limited in the first state 402. For example, at block 410, the system may permit and receive an operational parameter adjustment request. At block 412, optionally, if there are more than two states (third state is not shown in the diagram), the system may further perform a check. Provided that the second state 408 allows for adjustment of the optional parameter associated with the request, the system may proceed to block 414 where it adjusts the operational parameter accordingly.

The locking mechanism may work in concert with one or more components of a negative pressure treatment system. In another example, the system periodically interrogates the state of the locking mechanism instead of interrogating upon receipt of an adjustment request. Another example may be that the system may prompt a user provision of the authenticating input upon receiving adjustment requests. Yet another example may be that the locking mechanism does not remain in the second state 408, but prompts user authentication for every adjustment request.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A wound therapy apparatus comprising:
   a pressure source configured to provide negative pressure via a fluid flow path to a wound dressing and operate according to an operational parameter;
   a user interface configured to enable a user adjustment of the operational parameter; and
   a locking mechanism configured to:
      operate in at least two states comprising a first state in which a cover of the locking mechanism prevents the user adjustment of the operational parameter with the user interface and a second state in which the cover permits the user adjustment of the operational parameter with the user interface; and
      transition from the first state to the second state by retracting the cover or permitting removal of the cover responsive to a manipulation of the locking mechanism with a physical key or a match between an authentication input and an authentication key.

2. The wound therapy apparatus of claim 1, wherein in the first state, the locking mechanism is configured to physically prevent at least a portion of the user interface from receiving a user input to adjust the operational parameter.

3. The wound therapy apparatus of claim 1, wherein the locking mechanism is configured to transition from the first state to the second state by retracting the cover.

4. The wound therapy apparatus of claim 1, wherein the locking mechanism is configured to transition from the first state to the second state by permitting removal of the cover.

5. The wound therapy apparatus of claim 1, wherein the user interface is positioned in a compartment of a housing, and wherein the locking mechanism is configured to prevent access to the compartment when the locking mechanism is in the first state.

6. The wound therapy apparatus of claim 1, wherein the authentication input is provided via an electromagnetic transmission.

7. The wound therapy apparatus of claim 1, wherein the operational parameter comprises a pressure setpoint, a mode of operation setting, or a pump operation profile.

8. The wound therapy apparatus of claim 1, wherein the locking mechanism is configured to periodically verify the match between the authentication input and the authentication key.

9. The wound therapy apparatus of claim 1, wherein the locking mechanism is configured to transition from the second state to the first state responsive to a passage of a threshold time duration without the user interface receiving a user input at the user interface.

10. The wound therapy apparatus of claim 1, wherein the locking mechanism is configured to transition from the second state to the first state responsive to a passage of a threshold time duration without receiving a subsequent authentication input.

11. A kit comprising the wound therapy apparatus of claim 1 and the wound dressing.

12. A method of operating a negative pressure wound therapy apparatus, the method comprising:
   at a first time:
      providing negative pressure via a fluid flow path to a wound dressing with a pressure source operating according to an operational parameter; and
      with a locking mechanism that comprises a cover, preventing a user adjustment of the operational parameter with a user interface while the locking mechanism is in a first state; and
   at a second time:
      determining that an authentication input matches an authentication key;
      in response to determining that the authentication input matches the authentication key, transitioning the locking mechanism from the first state to a second state by retracting the cover or permitting removal of the cover;
      permitting the user adjustment of the operational parameter with the user interface while the locking mechanism is in the second state; and
      providing negative pressure via the fluid flow path to the wound dressing with the pressure source operating according to the operational parameter after the user adjustment of the operational parameter.

13. The method of claim 12, wherein preventing the user adjustment of the operational parameter with the user interface comprises physically preventing at least a portion of the user interface from receiving a user input to adjust the operational parameter.

14. The method of claim 12, further comprising, at a third time:

determining that a user input has not been received at the user interface over a threshold duration of time; and in response to determining that the user input has not been received at the user interface over the threshold duration of time, transitioning the locking mechanism from the second state to the first state.

15. The method of claim 12, further comprising, at a third time:

determining that a subsequent authentication input has not been received over a threshold duration of time; and in response to determining that the subsequent authentication input has not been received over the threshold duration of time, transitioning the locking mechanism from the second state to the first state.

16. The method of claim 12, further comprising, at a third time, periodically verifying the match of the authentication input and the authentication key.

17. A method of operating a negative pressure wound therapy apparatus, the method comprising:

at a first time:

providing negative pressure via a fluid flow path to a wound dressing with a pressure source operating according to an operational parameter; and with a locking mechanism that comprises a cover, preventing a user adjustment of the operational parameter with a user interface while the locking mechanism is in a first state; and at a second time:

detecting a manipulation of the locking mechanism with a physical key;

in response to detecting the manipulation of the locking mechanism with the physical key, transitioning the locking mechanism from the first state to a second state by retracting the cover or permitting removal of the cover;

permitting the user adjustment of the operational parameter with the user interface while the locking mechanism is in the second state; and providing negative pressure via the fluid flow path to the wound dressing with the pressure source operating according to the operational parameter after the user adjustment of the operational parameter.

18. The method of claim 17, further comprising, at a third time, transitioning the locking mechanism from the second state to the first state responsive to a removal of the physical key.

19. The method of claim 17, further comprising, at a third time:

determining that a user input has not been received at the user interface over a threshold duration of time; and in response to determining that the user input has not been received at the user interface over the threshold duration of time, transitioning the locking mechanism from the second state to the first state.

20. The method of claim 17, wherein preventing the user adjustment of the operational parameter with the user interface comprises physically preventing at least a portion of the user interface from receiving a user input to adjust the operational parameter.

* * * * *